(12) United States Patent
Ren et al.

(10) Patent No.: US 9,498,180 B2
(45) Date of Patent: Nov. 22, 2016

(54) DETECTING AND QUANTIFYING PATIENT MOTION DURING TOMOSYNTHESIS SCANS

(75) Inventors: Baorui Ren, Andover, MA (US); Loren Niklason, Tetonia, ID (US); Andrew Smith, Lexington, MA (US); Zhenxue Jing, Chadds Ford, PA (US); Jay Stein, Boston, MA (US)

(73) Assignee: HOLOGIC, INC., Bedford, MA (US)

( * ) Notice: Subject to any disclaimer, the term of this patent is extended or adjusted under 35 U.S.C. 154(b) by 24 days.

(21) Appl. No.: 13/198,352

(22) Filed: Aug. 4, 2011

(65) Prior Publication Data

US 2012/0033868 A1 Feb. 9, 2012
US 2015/0157288 A9 Jun. 11, 2015

Related U.S. Application Data

(60) Provisional application No. 61/370,892, filed on Aug. 5, 2010.

(51) Int. Cl.

| | |
|---|---|
| *G06K 9/00* | (2006.01) |
| *A61B 6/00* | (2006.01) |
| *A61B 6/02* | (2006.01) |
| *G06T 7/20* | (2006.01) |
| *A61B 5/055* | (2006.01) |
| *A61B 5/00* | (2006.01) |
| *A61B 6/03* | (2006.01) |
| *A61B 8/13* | (2006.01) |
| *A61B 8/08* | (2006.01) |
| *A61B 6/04* | (2006.01) |

(52) U.S. Cl.
CPC ............ *A61B 6/5264* (2013.01); *A61B 5/055* (2013.01); *A61B 5/7207* (2013.01); *A61B 6/025* (2013.01); *A61B 6/035* (2013.01); *A61B 6/461* (2013.01); *A61B 6/481* (2013.01); *A61B 6/502* (2013.01); *A61B 6/5223* (2013.01); *A61B 8/13* (2013.01); *A61B 8/5276* (2013.01); *G06T 7/2033* (2013.01); *A61B 6/0414* (2013.01); *G06T 2207/10112* (2013.01); *G06T 2207/30068* (2013.01)

(58) Field of Classification Search
USPC .................................. 382/103, 130, 131, 132
See application file for complete search history.

(56) References Cited

U.S. PATENT DOCUMENTS

| | | | | |
|---|---|---|---|---|
| 7,433,507 | B2 * | 10/2008 | Jabri et al. ..................... | 382/132 |
| 2008/0242968 | A1 * | 10/2008 | Claus et al. .................. | 600/407 |
| 2009/0129556 | A1 * | 5/2009 | Ahn .............................. | 378/208 |
| 2009/0262887 | A1 * | 10/2009 | Iordache et al. ................ | 378/37 |

(Continued)

OTHER PUBLICATIONS

Siewerdsen et al., "A simple, direct method for x-ray scatter estimation and correction in digital radiography and cone-beam CT," Med. Phys. 33(1), Jan. 2006.*

(Continued)

*Primary Examiner* — Soo Park
(74) *Attorney, Agent, or Firm* — Kriegsman & Kriegsman

(57) ABSTRACT

The effects of patient motion in tomosynthesis scan images are automatically detected and quantified. In at least one embodiment an indication of detection of the effects of patient motion in tomosynthesis scan images is provided shortly after the scan, e.g., before the patient is discharged or before the breast is decompressed. A patient motion score may be calculated as part of motion quantification. The score may be stored for subsequent retrieval. Images may be presented with reference features to help a technician confirm of the effects of motion in images.

35 Claims, 10 Drawing Sheets

(56) References Cited

U.S. PATENT DOCUMENTS

| | | | |
|---|---|---|---|
| 2009/0274272 A1* | 11/2009 | Stanton et al. | 378/62 |
| 2010/0054630 A1* | 3/2010 | Avinash et al. | 382/294 |
| 2010/0329514 A1* | 12/2010 | Mundry | 382/107 |
| 2011/0123084 A1* | 5/2011 | Sebok | 382/132 |

OTHER PUBLICATIONS

Ren et al. "Automatic patient motion detection in digital breast tomosynthesis", Medical Imaging 2011: Physics of Medical Imaging, Mar. 16, 2011.*

* cited by examiner

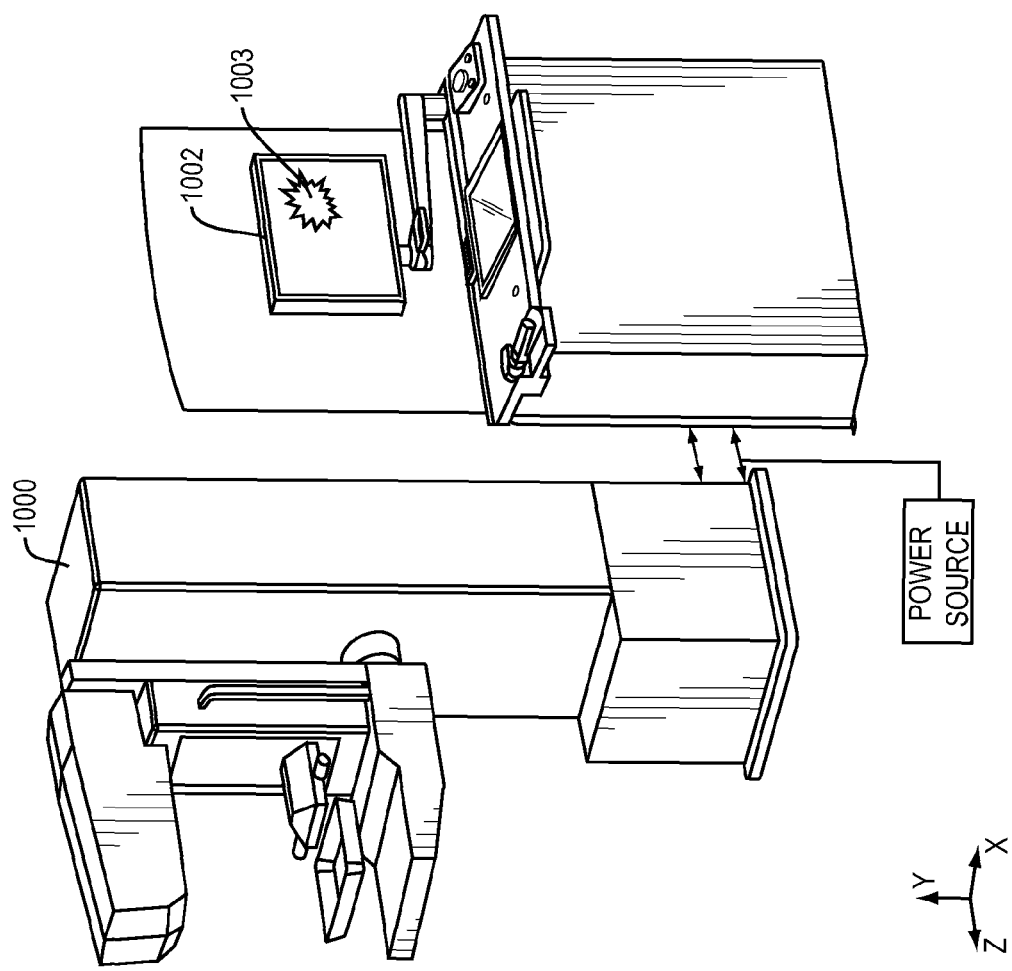

DETECTING AND QUANTIFYING PATIENT MOTION DURING TOMOSYNTHESIS SCANS

CROSS-REFERENCE TO RELATED APPLICATIONS

A claim of priority is made to U.S. Provisional Patent Application Ser. No. 61/370,892, filed Aug. 5, 2010, entitled SYSTEM AND METHOD FOR DETECTING PATIENT MOTION DURING TOMOSYNTHESIS SCANS, which is incorporated by reference.

BACKGROUND

X-ray screening exams are used to detect breast cancer and other diseases. Efforts to improve the sensitivity and specificity of breast x-ray systems have lead to the development of tomosynthesis systems. Breast tomosynthesis is a three-dimensional imaging technology that involves acquiring images of a stationary compressed breast at multiple angles during a short scan. The individual images are reconstructed into a series of thin, high-resolution slices that can be displayed individually or in a dynamic ciné mode. Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. Nos. 7,245,694 and 7,123,684, commonly owned by the Assignee of this application.

In order to facilitate screening and diagnosis with tomosynthesis systems it is generally desirable to obtain high quality images. One cause of degradation of image quality is patient motion during the tomosynthesis scan. Patient motion tends to cause blurring of one or more of the images. The blurring can be severe enough to render the associated images unacceptable for clinical screening or diagnosis. Further complicating the problem, the tomosynthesis images obtained during a scan might not be analyzed until after the patient's breast has been decompressed and the patient has been discharged. As a result, the patient must be called back for a new scan due to severe image blurring, thereby increasing patient frustration and anxiety, and potentially delaying diagnosis of malignancies.

SUMMARY

In accordance with one aspect of the invention an apparatus comprises: an image acquisition mechanism that generates a plurality of images of an imaging target in a time series during a scan; an image processor that processes the images; a computer which detects motion of the target during the scan by comparing an actual location of at least one point of reference in each individual processed image with an expected location of the at least one point of reference derived from a set of the processed images; and a mechanism for prompting a responsive action if motion is detected.

In accordance with another embodiment of the invention a method comprises: generating a plurality of images of an imaging target in a time series during a scan; processing the images; using a computer, detecting motion of the target during the scan by comparing an actual location of at least one point of reference in each individual processed image with an expected location of the at least one point of reference derived from a set of the processed images; and prompting a responsive action if motion is detected.

Timely automatic detection and quantification of patient motion can prompt a screening technician to repeat a compromised scan before patient is discharged, or even before the breast is decompressed. This advantageously mitigates patient frustration and anxiety, and also reduces diagnostic delays. Moreover, the results can be used to enhance image processing. These and other features and advantages will be more completely understood in light of the detailed description.

BRIEF DESCRIPTION OF THE DRAWINGS

FIGS. 8a and 8b illustrates a system capable of providing an indication to the technician if the motion score exceeds a predetermined threshold.

DETAILED DESCRIPTION

One embodiment of the invention includes automatically detecting the effects of patient motion in time-series scan images, e.g., tomosynthesis images. Another embodiment of the invention includes providing an indication of detection of the effects of patient motion in tomosynthesis scan images, possibly shortly after the scan, e.g., before the patient is discharged or before the breast is decompressed. Another embodiment of the invention includes calculating a patient motion score. Another embodiment of the invention includes presenting images with reference features to help a technician confirm of the effects of motion in images. These and other embodiments of the invention are described in greater detail below.

Baorui Ren et al., "Automatic patient motion detection in digital breast tomosynthesis," Medical Imaging 2011: Physics of Medical Imaging, Proc. of SPIE Vol. 7961 7961 5F, (2011) is incorporated by reference.

Figure 1A:
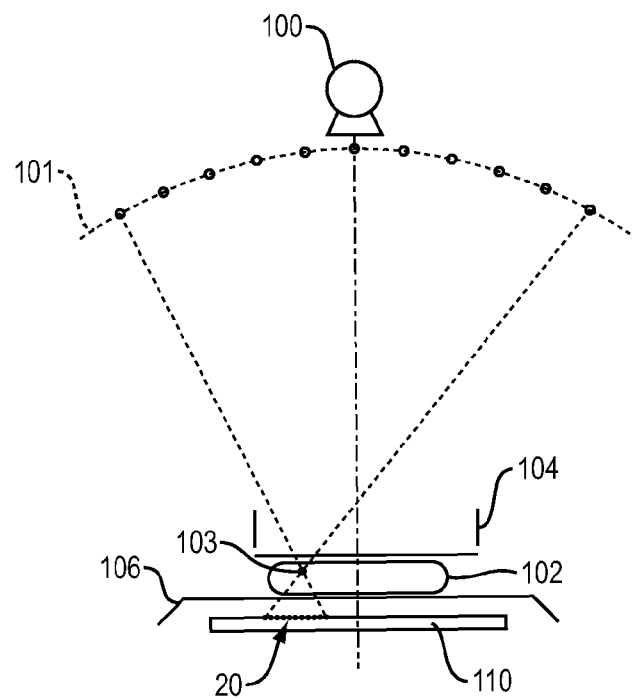
FIG. 1a illustrates use of a feature to detect patient motion.

Referring to FIG. 1a, during a tomosynthesis scan a patient's breast 102 is immobilized between a compression paddle 104 and a breast platform 106. An x-ray receptor 110 is disposed within a housing located below the breast platform 106. An x-ray source 100 moves along an arc 101 which may be centered on the top surface of the receptor 110. At predetermined discrete positions source 100 is energized to emit a collimated x-ray beam, for example and without limitation, at every 1.07° of an arc of +/−7.5°. The beam irradiates the breast 102, and radiation that has passed through the breast is received by receptor 110. Receptor 110 and associated electronics generate image data in digital form for each pixel of a rectangular grid of pixels at each predetermined discrete angular position of source 100.

The motion of source 100 can be continuous or discontinuous. If motion is continuous, a respective set of image data is accumulated over a small increment of continuous motion, e.g., a 0.1° to 0.5° arc of motion of source 100, although these non-limiting parameters are only an example. Different ranges of motion of the source 100 can be used, and the motion of the source 100 may be along an arc centered at a different axis, such as inside immobilized breast 102 or at breast platform 106 or at receptor 110. Furthermore, source motion is not necessarily along an arc, and can be translational or a combination of different types of motions, such as partly translational and partly rotational.

Figure 1B:
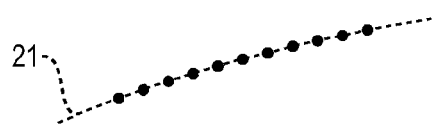
FIG. 1b illustrates projection of a feature that is not affected by patient movement.

Referring to FIGS. 1a and 1b, a distinct feature 103 of the breast will project onto the detector at a different position for each different image, resulting in a projection path 20, because the x-ray source position is different for each image. Furthermore, a projection path 21 among all view angles generally follows a smooth trajectory for a tomosynthesis scan which is free of patient motion because of the way x-ray source motion is defined, e.g., in a controlled arc, and because x-ray exposures are taken in a temporally and spatially uniform manner. However, the projection of the feature will not follow a smooth trajectory if the patient moves during the scan.

Figure 1C:
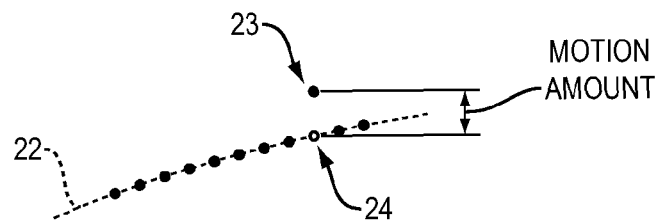
FIG. 1c illustrates projection of a feature that is affected by patient movement.

FIG. 1c illustrates a projection path 22 where an image is affected by patient movement. In one image the actual position 23 of the feature differs from the expected position 24 of the feature. The difference between the actual position 23 and the expected position 24 is indicative of the magnitude of patient motion. Consequently, features such as introduced markers, lesions, calcifications, masses and other artifacts in or on the x-rayed object can be used to detect patient motion and calculate an indication of the magnitude (severity) of the motion, e.g., using a computer with processors, non-transitory memory and a computer program product which receives various inputs, performs various calculations, and provides outputs such as described in this application.

Figure 2A:
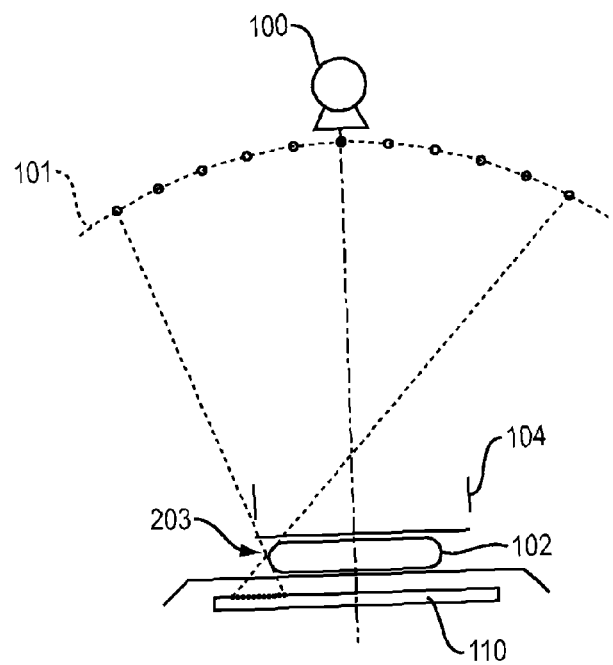
FIG. 2a illustrates use of an edge line feature to detect patient motion.
Figure 2B:
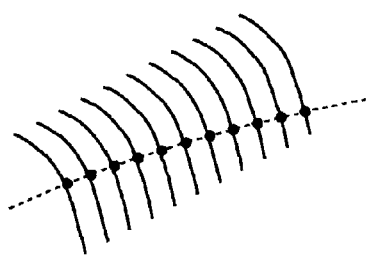
FIG. 2b illustrates projection of an edge line that is not affected by patient movement.
Figure 2C:
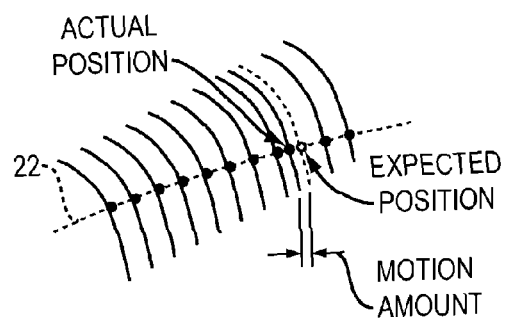
FIG. 2c illustrates projection of an edge line that is affected by patient movement.
Figure 3:
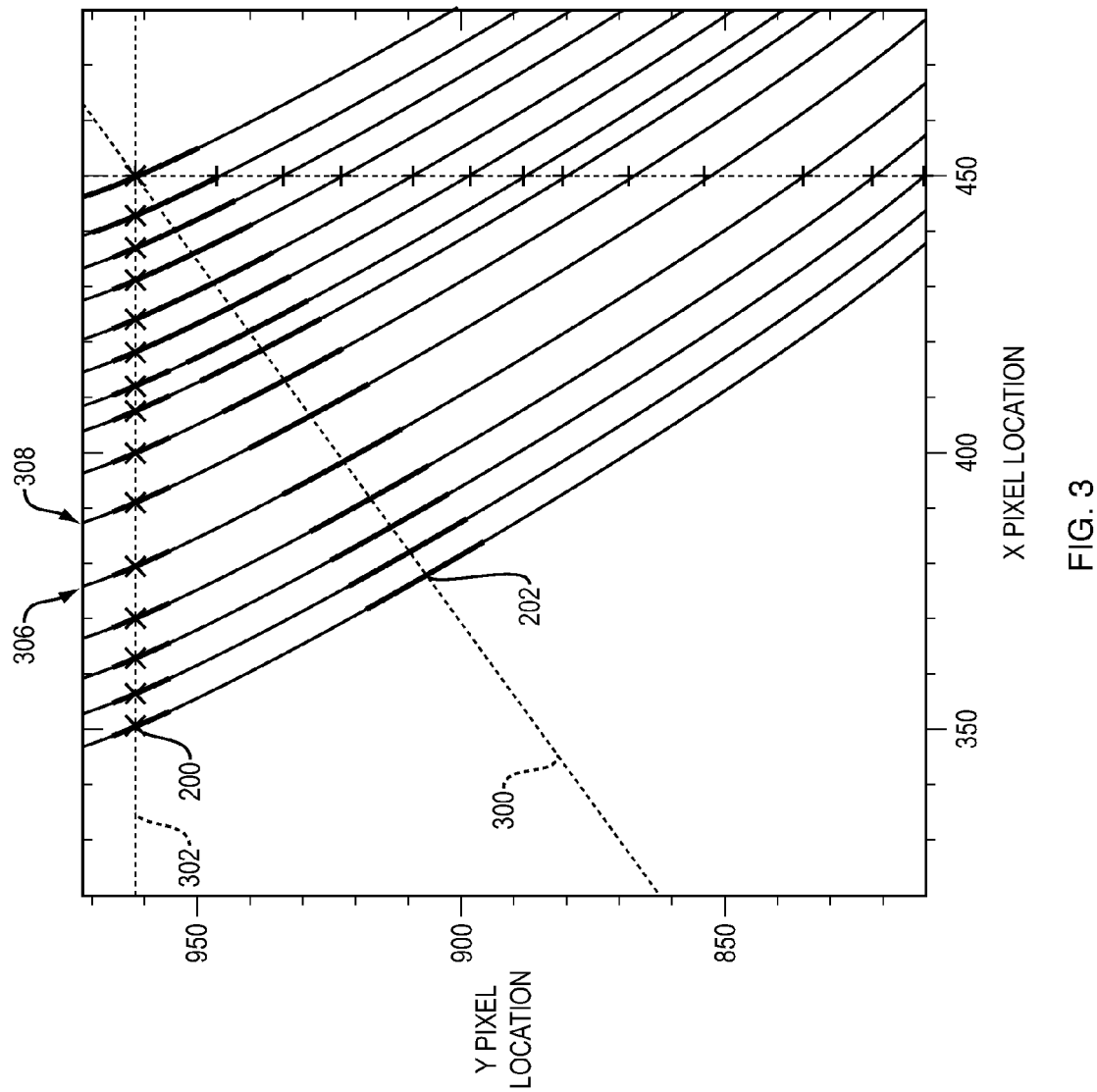
FIG. 3 illustrates displacement of selected locations of the series of breast skin line images.

Referring to FIGS. 2a, 2b, 2c and 3, patient motion can also be detected in a series of images based on displacement of an edge line such as the skin line of the breast, an implant edge, or some other internal edge. In order to utilize an edge line such as skin line 203 to detect motion, locations along the edge line are selected, e.g., five points at each side of the nipple in a projection image. Location 200 is an example, but it should be noted that the present invention is not limited to any particular number or arrangement of locations. The locations can be selected in one image and then used to calculate positions of the corresponding locations in other images. For example, a line 300 which intersects a location 202 and is orthogonal to the skin line in a first image will intersect the skin line of a second image at the first location of the second image. A non-orthogonal line 302 could alternatively be used. The relative displacement of the locations between N skin lines associated with N projection images is calculated, e.g., along the normal direction of the skin line at each location. FIG. 2b illustrates projection of an edge line that is not affected by patient movement, as indicated by coincidence of expected and actual positions of the selected location along the edge line. FIG. 2c illustrates projection of an edge line that is affected by patient movement, as indicated by displacement (motion amount) between the expected position of the selected location and the actual position of the selected location in one image.

Some displacement is expected due to motion of the x-ray source. However, the rate of change of displacement should define a smooth curve in the absence of patient motion. Consequently, the rate of change of displacement can also be used to detect patient motion.

Figure 4:
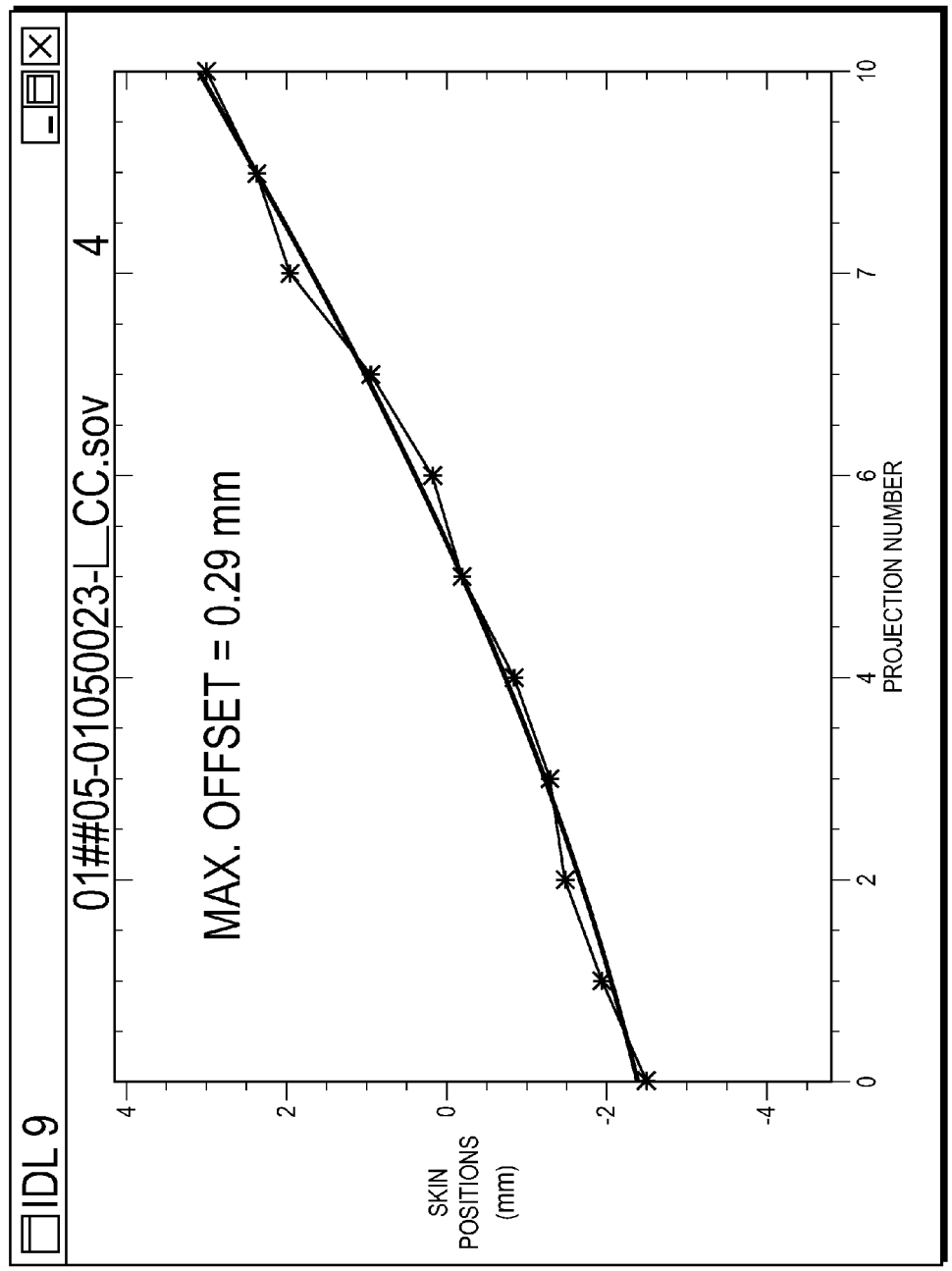
FIG. 4 illustrates a $2^{nd}$ order curve fitted to the selected locations.
Figure 5:
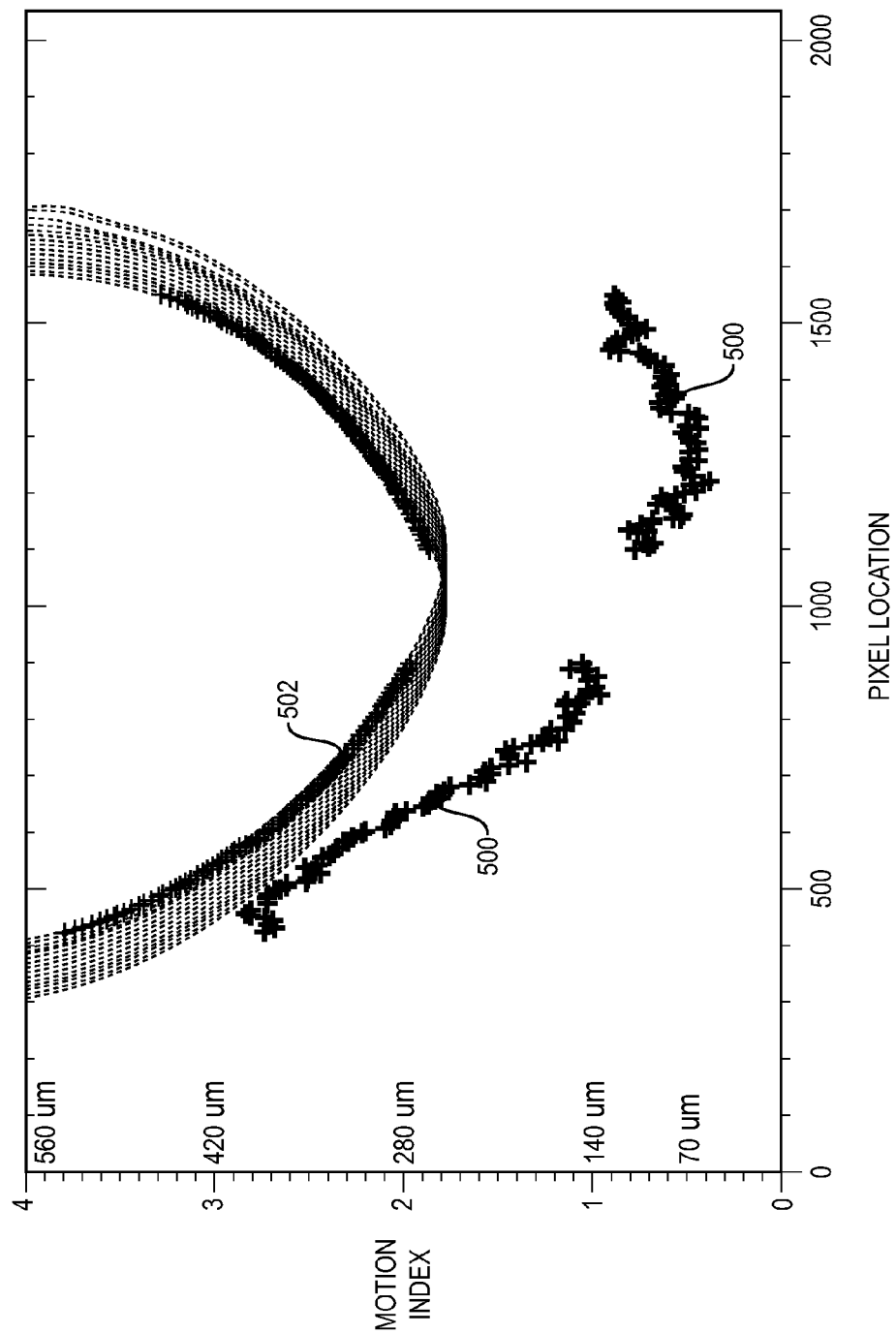
FIG. 5 illustrates a plot of maximum deviations at two segments of locations along the compressed breast edge in a case of relatively severe breast motion.
Figure 6:
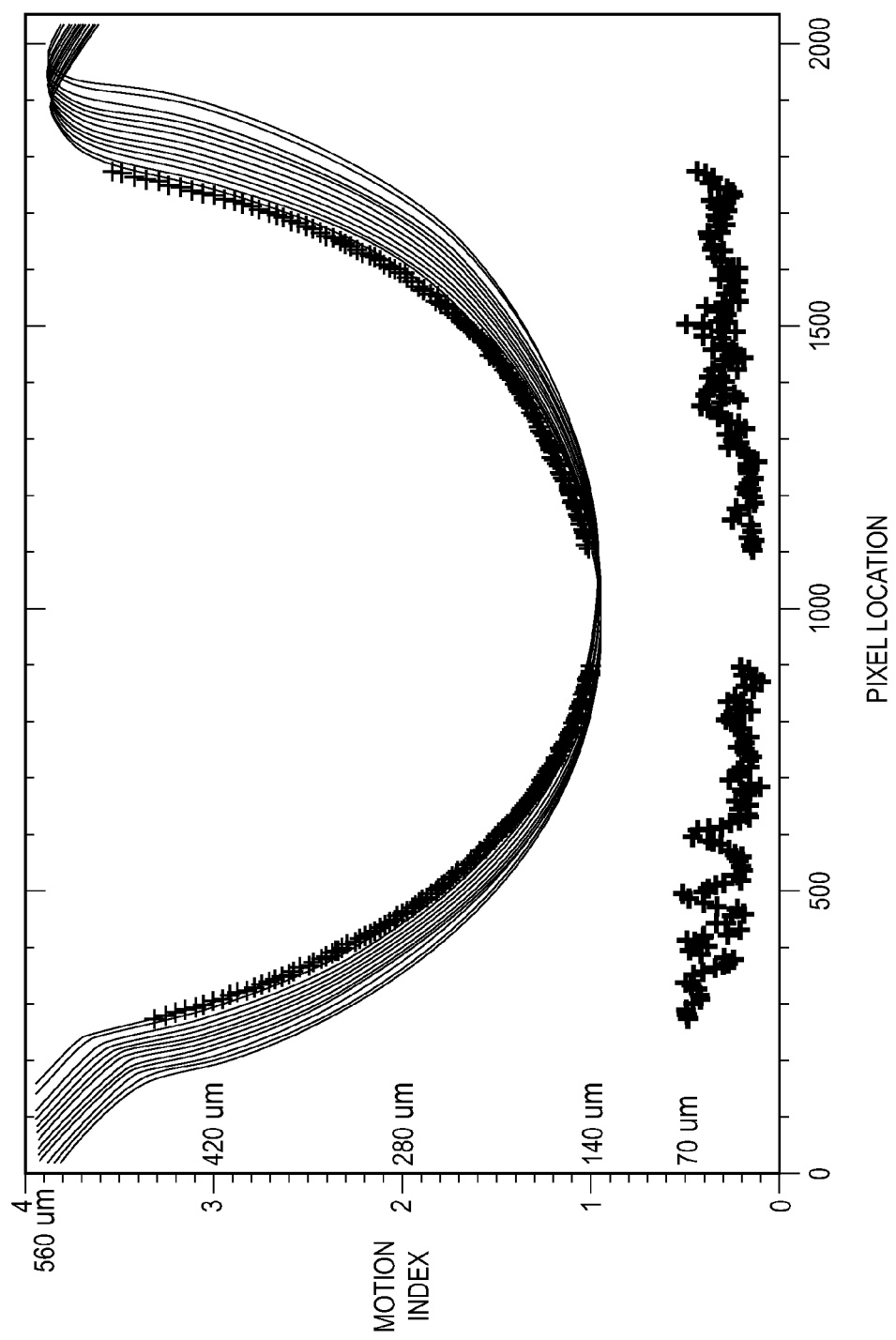
FIG. 6 illustrates a plot of maximum deviations at two segments of locations along the compressed breast edge in a case of relatively minimal breast motion.

Referring to FIG. 4, one way to detect the presence of patient motion and calculate the magnitude of that motion is to fit a $2^{nd}$ order curve to the locations/features of each image. The deviation of each location/feature from the expected location on the $2^{nd}$ order polynomial fitting curve is then calculated. The maximum deviation is recorded as the motion amount of the feature or skin line at the analysis location. An example of severe breast motion is shown in FIG. 5, where the magnitude of motion 500 is superimposed over the edge lines 502 from which the magnitude is calculated. The horizontal axis of the graph is the pixel location of skin lines along the chest wall direction of patient, while the vertical axis is the motion distance in unit of micron and in unit of number of detector pixel. It can be seen that the motion is greater on one side of the breast, in this example on the side with pixel locations <1000. An example with minimal motion is shown in FIG. 6.

The severity of patient motion may be used to automatically calculate a motion score. The motion score can be correlated to the displacement amount in selected units, e.g., in mm, where the displacement is the deviation of the feature from the expected position or of the skin line positions from the smooth curve. The maximum deviation of the curve is recorded as the breast motion amount, or displacement, at the sampled location. The motion score may then be calculated by averaging the absolute values of the displacement amounts across the projection images, taking a maximum displacement amount for any point along the project path, or with various other techniques of using the displacement amounts to determine a motion score. Such techniques will be readily apparent to those skilled in the art.

Figure 7:
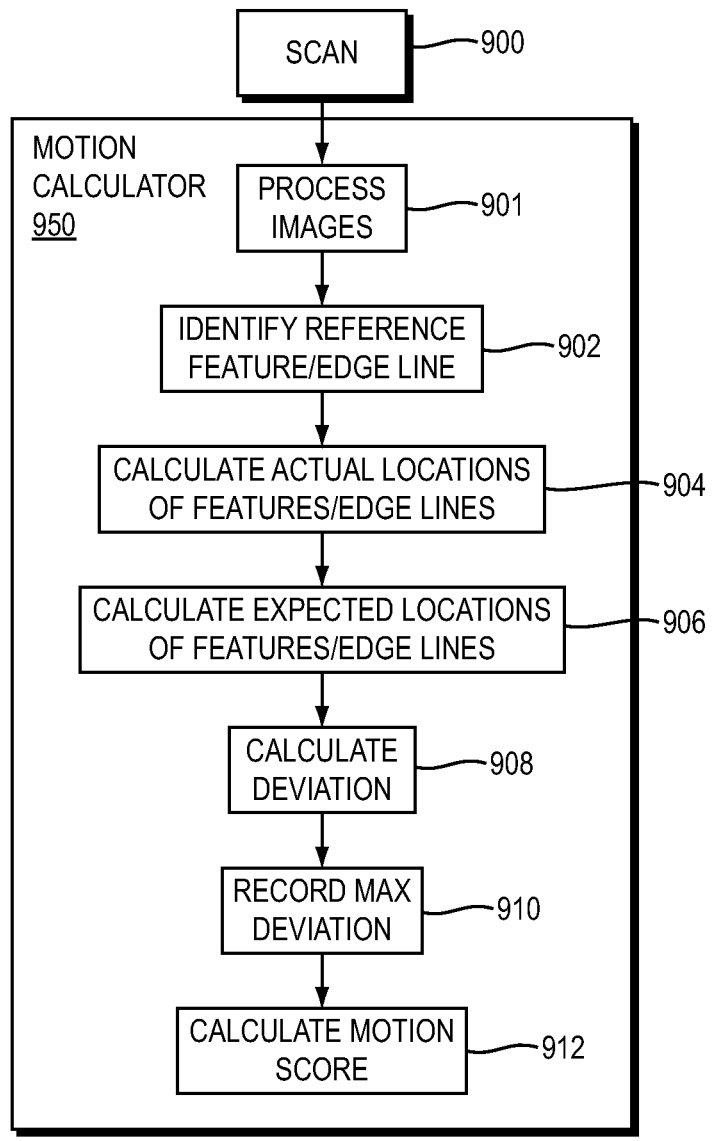
FIG. 7 illustrates a method for detecting and quantifying patient motion during a tomosynthesis scan.

Referring to FIG. 7, a method of detecting and quantifying patient motion begins with a scan 900 in which multiple images are obtained in time-series. The images are then transformed, reconstructed or otherwise processed to generate one or more images that can be utilized to detect motion as indicated by step 901. The result may be, for example, the same or a different number of projection images or reconstructed slices. The next step 902 is to identify a reference feature or reference points on an edge line associated with the breast. The actual locations of the features/edge line reference points associated with N images of the breast are then calculated in step 904. The expected locations of the features/edge line reference points associated with the N images of the breast are then calculated in step 906. The step can include, for example, fitting a $2^{nd}$ order (or other order) curve to the features/edge line reference points of all or a subset of images. Furthermore, the process may be iterative. For example, the number of images in the subset may be changed in different iterations. Also, different fitting models may be utilized in different iterations. Iteration may be stopped when predetermined conditions are satisfied. The deviation of each feature/edge line reference point from the expected location is then calculated in step 908. The maximum deviation is recorded as the motion amount of the feature or skin line at the analysis location in step 910. The process then continues with another qualified feature/edge line location, until multiple features/edge line locations have been processed in order to analyze the entire breast volume/skin line for motion. The motion score of the entire breast may then be calculated in step 912. The entire algorithm for calculating the motion score is identified as group 950.

Figure 8B:
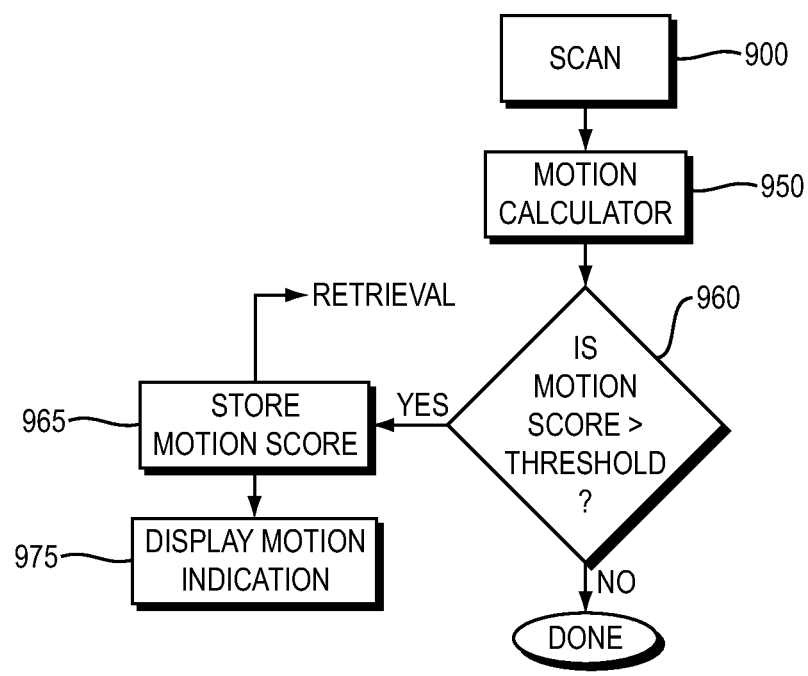

Referring to FIGS. 8*a* and 8*b*, an indication is provided to the technician if the motion score exceeds a predetermined threshold. The scan 900 is followed by the Motion Calculator 950. The motion score 912 is compared to a predefined threshold, and if exceeded, the motion score is stored in step 965 and a display or other indication 1003 is presented to the user in step 975. The motion score may be stored in one or more of various formats for subsequent retrieval. There are a variety of Picture Archiving and Communication Systems (PACS) which store images. It is envisioned that PACS could store patient data including motion score in a non-transitory computer-readable memory. The motion indicator provided to the technician may include displaying a signal, icon, numerical score or other visual or auditory representation of patient motion on a user interface of the tomosynthesis system, e.g., on the gantry 1000 or on a workstation 1002 coupled to the gantry for viewing by a radiologist. The indicator may simply indicate that the threshold has been reached. Alternatively, the indicator may convey severity of motion to the technician, e.g., using a numerical score or a watermark, varying an intensity of a visual indicator, etc., to enable the technician to selectively obtain an additional scan depending upon the degree of potential image degradation based on patient motion. In addition, the indicator, or motion score, may be stored in a dicom header or other field of patient data, saved to a database, and used by image processing tools such as a Computer Assisted Detection system with motion score incorporated and CAD decision optimized because of it (CAD application).

Detection of patient motion and severity may be used to enhance the tomosynthesis system by prompting action by the operator. For example, in response to an exceeded threshold, the technician may immediately re-take the tomosynthesis images, perhaps before the patient is dismissed. A scan may be deemed acceptable by the operator if the motion score is below the threshold, although some amount of patient motion has been detected. The operator may also manually select images for removal from processing and reconstruction to improve the image quality of final reconstruction slices. The motion detection can take place in real time, or at some later time after the patient has left or the operator is finished with the procedure.

Motion analysis may also be used to automatically adjust or dispose of images most affected by patient motion. For example, if a subset of the images exhibit motion, image reconstruction might be performed without that subset of images that have been affected by motion, or performed with all images after correction has been applied to the affected subset of images. Such motion-score based processing may include proper global and local adjustment, transformation, and, shift back to correct the motion amount. In addition, motion scores could be used to prompt and perform filtering to suppress the high-frequency content (edges, calcs) to prevent contamination (blurring) of the final image while passing the low frequency content to improve the signal to noise ratio of final images.

Figure 9:
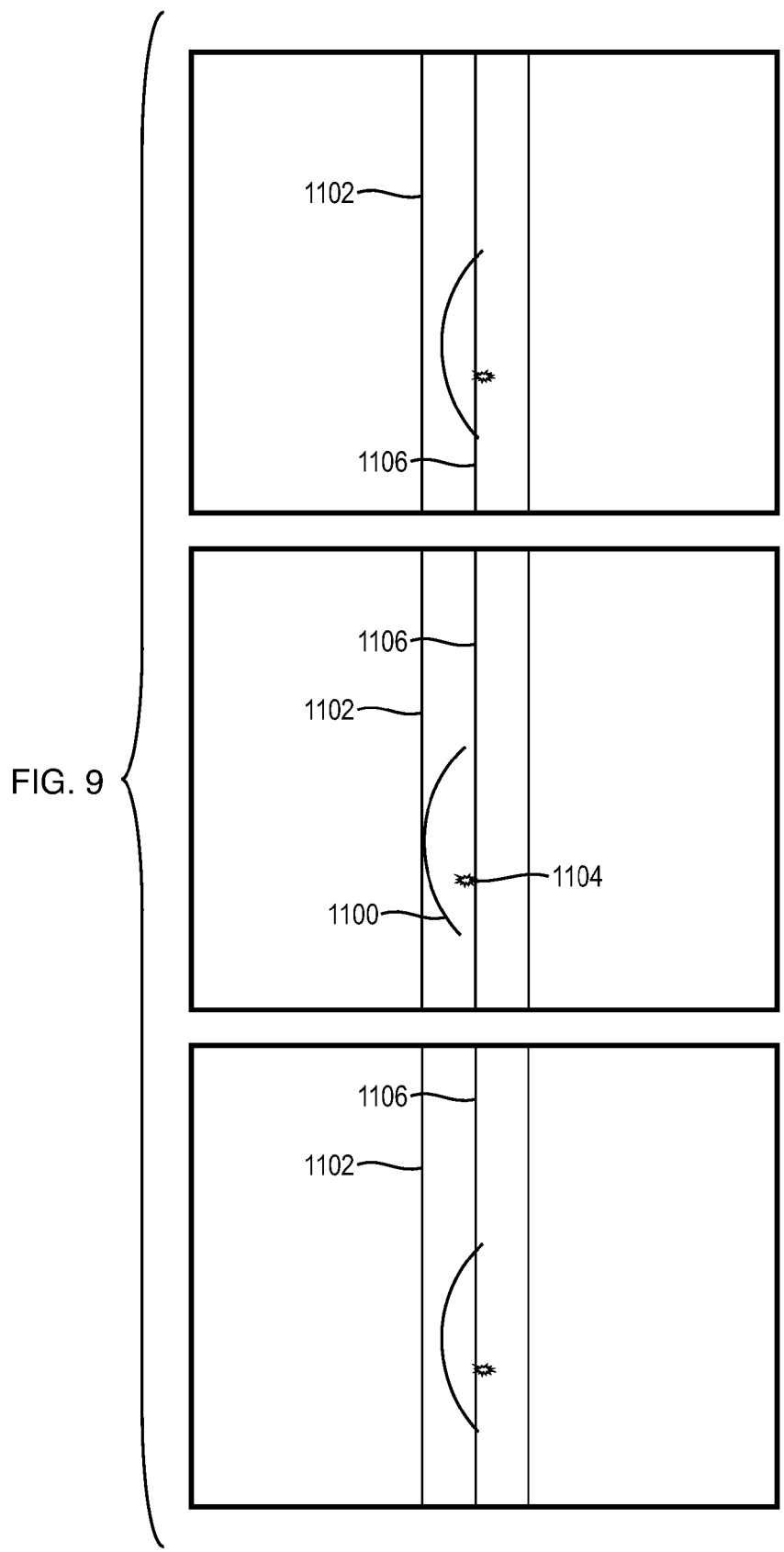
FIG. 9 illustrates presentation of images with reference features to help a technician confirm of the effects of motion in images.

Referring to FIG. 9, a set of images may be presented on the user interface to enable the technician to confirm the presence of patient motion. For example, the images may be presented in ciné mode with stationary reference lines or other features superimposed over the images on the display monitor. The reference lines or features facilitate visual confirmation of motion. For example, the distance between a nearby reference line and a distinct feature of the image may be seen to change in ciné mode. Motion is indicated in the second image of the three successive images in FIG. 9 by intersection of the skin line 1100 with the reference line 1102, and also by traversal of reference line 1106 by lesion 1104. In practice it may be desirable to superimpose multiple parallel reference lines oriented with respect to the breast image such that the reference lines are orthogonal to the direction is most likely patient motion.

It is envisioned that motion detection and quantification may be performed using reconstructed slice images although the above methods of tracking artifacts have described comparison of sequential projection images. In tomosynthesis reconstruction the projections images are summed after shifting and transforming one relative to another in a specific way (referred as component images) to produce a reconstruction slice that reinforces the spiculated lesion object located at the height of that slice in a breast and reduces the contrast of other objects located away from the slice by blurring them out. One technique for performing motion detection and quantification using reconstructed slice images is to compare individual locations in the component images with the reconstructed slice image at the height at which the feature is in focus. The difference between locations in each individual component image versus the location in the reconstruction slice is used as the displacement in the calculations described above. Another example is to utilize a slice where the selected feature is out of focus. In such a case the locations of the selected feature appears as a trajectory cluster (epi-polar curve), so the analysis is performed by finding the location of each member of the cluster individually, and then finding the expected location of that member. Accordingly the visual confirmation method depicted in FIG. 9 can also be applied to review tomosynthesis reconstruction slices by co-displaying reference lines superimposed on display monitor. Such alternative embodiments are therefore within the scope of the present invention. Furthermore, although the above description has dealt largely with detecting patient motion during tomosynthesis imaging for the purpose of predicting image quality, it can easily be appreciated how the principles of the present invention may be extended beyond the tomosynthesis modality to any imaging modality which acquires at least two images of an object over an extended time period. Such modalities include, but are not limited to, Computed Tomography (CT) scans, Positron Emission Tomography (PET) scans, Single Photon Emission Computed Tomography (SPECT) scans, ultrasound image acquisition, contrast enhanced imaging, and Magnetic Resonance Imaging (MRI). Thus, the present invention may be used for any time-series of image acquisition system to identify any abnormal changes between sequenced images attributable to patient motion during the acquisition. Motion detection and analysis can also be included as part of system QC test; if mechanical component is malfunctioning, it would generate a non-zero motion score from phantom scan and help identify the problem in the mechanical system.

Accordingly, a system, apparatus, method and computer program have been described for detecting and quantifying motion of an object or a component of the motion of the object by evaluating displacement of a feature within a series of images acquired over a time period. The feature may be, without limitation, a skin line, internal edge line, internal object such as calcification, lesion, mass or other object, or an external marker. Any one of a variety of imaging modalities may be used, and the quantified motion may be displayed in any variety of manners, including but not limited to on the acquisition device, on technologist workstation, and in a dicom header. The quantified motion may be used to generate a motion score, prompt re-acquisition of images, as an input to an image processing stage of a reconstruction algorithm, and as an input to a CAD processing system.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

The invention claimed is:

1. Apparatus comprising:
an image acquisition mechanism that generates a plurality of images of an imaging target of an individual in a time series during a scan;
an image processor that processes the plurality of images to generate processed images, wherein the processed images are at least one of projection images and reconstructed images;
a computer which is configured to display the processed images and which detects and quantifies motion of the target of a magnitude of between about 70 μm to about 420 μm during the scan by comparing an actual location of at least one point of reference in each processed image with an expected location of the at least one point of reference derived from a set of the processed images and by generating a motion score, wherein the at least one point of reference is an intrinsic marker of the individual and wherein the intrinsic marker comprises a plurality of points along a skin line; and
a mechanism for comparing the motion score to a threshold and for prompting a responsive action if the motion score exceeds the threshold.

2. The apparatus of claim 1 wherein the image processor enhances a set of the plurality of images or generates a mathematically transformed projection image.

3. The apparatus of claim 1 wherein the computer estimates the expected locations of the at least one reference point in successive images.

4. The apparatus of claim 3 wherein the computer calculates the expected locations by fitting a curve to each reference point location or by averaging.

5. The apparatus of claim 1 wherein the computer quantifies motion based on maximum displacement of the reference point.

6. The apparatus of claim 1 wherein the motion score is calculated using weighted average, max, median, min, or other operation.

7. The apparatus of claim 1 wherein an indication is provided to a technician if the motion score exceeds a predetermined threshold.

8. The apparatus of claim 7 wherein the indication includes at least one of a signal, icon, numerical score or other visual or auditory representation of patient motion displayed on a user interface of a gantry or workstation.

9. The apparatus of claim 7 wherein the indication is stored in a dicom header or other field of patient data.

10. The apparatus of claim 1 wherein the responsive action includes automatically adjusting or disposing of an image.

11. The apparatus of claim 1 wherein a set of images is presented on an interface with at least one reference feature to enable confirmation of motion.

12. The apparatus of claim 1 wherein the computer selectively discards or mathematically corrects a portion of projection data during image reconstruction.

13. The apparatus of claim 1 wherein the image acquisition mechanism is selected from a group of image acquisition systems which acquire images using tomosynthesis, a Computed Tomography (CT) image acquisition system, a PET, SPECT, Ultrasound, Contrast Enhanced, and MRI.

14. The apparatus of claim 1 wherein the image acquisition mechanism is a digital breast tomosynthesis system.

15. Apparatus comprising:
an image acquisition mechanism that generates a plurality of images of an imaging target of an individual in a time series during a scan;
an image processor that processes the images;
a computer which detects motion of the target during the scan by comparing an actual location of at least one point of reference in each processed image with an expected location of the at least one point of reference derived from a set of the processed images, wherein the at least one point of reference is an intrinsic marker of the individual along a skin line, wherein the intrinsic marker comprises a plurality of points along the skin line, and wherein the computer calculates displacement of the at least one reference point between N skin lines associated with N images along a selected direction relative to the N skin lines; and
a mechanism for prompting a responsive action if motion is detected.

16. The apparatus of claim 15 wherein the computer quantifies motion based on change of displacement or rate of change of displacement of the at least one reference point.

17. The apparatus of claim 16 wherein the computer quantifies motion based on maximum displacement of the reference point.

18. A method comprising:
generating a plurality of images of an imaging target of an individual in a time series during a scan;
processing the plurality of images to generate processed images, wherein the processed images are at least one of projection images and reconstructed images;
using a computer, detecting and quantifying motion of the target of a magnitude of between about 70 μm to about 420 μm during the scan by comparing an actual location of at least one point of reference in each processed image with an expected location of the at least one point of reference derived from a set of the processed images and by generating a motion score, wherein the at least one point of reference is an intrinsic marker of the individual and wherein the intrinsic marker comprises a plurality of points along a skin line; and
comparing the motion score to a threshold and prompting a responsive action if the motion score exceeds the threshold.

19. The method of claim 18 including enhancing a set of the plurality of images or generating a mathematically transformed projection image.

20. The method of claim 18 including estimating the expected locations of the at least one reference point in successive images.

21. The method of claim 20 including calculating the expected locations by fitting a curve to each reference point location or by averaging.

22. The method of claim 18 including quantifying motion based on maximum displacement of the reference point.

23. The method of claim 18 including calculating the motion score using weighted average, max, median, min, or other operation.

24. The method of claim 18 including providing an indication to a technician if the motion score exceeds a predetermined threshold.

25. The method of claim 24 including providing an indication with at least one of a signal, icon, numerical score or other visual or auditory representation of patient motion displayed on a user interface of a gantry or workstation.

26. The method of claim 24 including storing the indication in a dicom header or other field of patient data.

27. The method of claim 18 including automatically adjusting or disposing of an image as a responsive action.

28. The method of claim 18 including presenting a set of images on an interface with at least one reference feature to enable confirmation of motion.

29. The method of claim 18 including selectively discarding or mathematically correcting a portion of projection data during image reconstruction.

30. The method of claim 18 including generating the images using an image acquisition mechanism selected from a group of image acquisition systems which acquire images using tomosynthesis, a Computed Tomography (CT) image acquisition system, a PET, SPECT, Ultrasound, Contrast Enhanced, and MRI.

31. The method of claim 18 including storing information indicative of patient motion.

32. The method of claim 18 wherein the plurality of images is generated using a digital breast tomosynthesis system.

33. A method comprising:
generating a plurality of images of an imaging target of an individual in a time series during a scan;
processing the images;
using a computer, detecting motion of the target during the scan by comparing an actual location of at least one point of reference in each processed image with an expected location of the at least one point of reference derived from a set of the processed images, wherein the at least one point of reference is an intrinsic marker of the individual along a skin line, wherein the intrinsic marker comprises a plurality of points along the skin line, and wherein said detecting step includes calculating displacement of the at least one reference point between N skin lines associated with N images along a selected direction relative to the N skin lines; and
prompting a responsive action if motion is detected.

34. The method of claim 33 including quantifying motion based on change of displacement or rate of change of displacement of the at least one reference point.

35. The method of claim 34 including quantifying motion based on maximum displacement of the reference point.

* * * * *